United States Patent [19]

Miclo et al.

[11] Patent Number: 5,846,939
[45] Date of Patent: Dec. 8, 1998

[54] USE OF A DECAPEPTIDE WITH BENZODIAZEPINE-TYPE ACTIVITY FOR PREPARING MEDICINES AND FOOD SUPPLEMENTS

[75] Inventors: Laurent Miclo, Nancy; Emmanuel Perrin, Saulxures-Les-Nancy; Alain Driou, Laxou; Jean-François Boudier, Agny; Catherine Iung, Paris; Guy Linden, Heillecourt, all of France

[73] Assignee: Societe Cooperative Agricole Laitiere D'Artois Et Des Flandres, La Prosperite Feriere, Arras, France

[21] Appl. No.: 562,979

[22] Filed: Nov. 27, 1995

[30] Foreign Application Priority Data

Nov. 30, 1994 [FR] France ................... 94 14362

[51] Int. Cl.[6] .................................................. A61K 38/08
[52] U.S. Cl. ............................................. 514/15; 530/328
[58] Field of Search ............................... 514/15; 530/328; 435/213

[56] References Cited

U.S. PATENT DOCUMENTS 5,208,240  5/1993  Peet et al. ................................ 514/263

FOREIGN PATENT DOCUMENTS 06239888  2/1993  Japan .

OTHER PUBLICATIONS

Minawawa et al. 'Dibittering mechanism in bitter peptides of enzymatic hydrolysates from milk casein by aminopeptidase T', J. of Food Sci., 54(5), pp 1225–1229 Oct. 1989.

Shon et al. 'Antibodies raised against peptide fragments of bovine s1—casein cross–react with the native protein, but recognize sites distinct from the determinants on the protein', Eur. J. Immunol., 21, pp. 1475–1480 1991.

Yan et al., 'Purification and characterization of a novel metalloendopeptidase from *Steptococcus cremoris* H61', Eur. J. Biochem. 163, pp. 259–265 1987.

Niles et al., 'Pharmacological inhibition fo Forskolin–stimulated adenylate cyclase activity in rat brain melatonin, its analogs, and diazepam.' Biochem. Pharmac., 40(12), pp. 2701–2705 1990.

Loukas et al. 'Opioid acivities and structures of –Casein–Derived Exophins.' Biochemistry, 22, 4567–4573 1983.

Copy of European Search from French patent94/14362, filed Nov. 30, 1994 with cited references.

*Primary Examiner*—Cecilia J. Tsang
*Assistant Examiner*—Anish Gupta
*Attorney, Agent, or Firm*—Wolf, Greenfield & Sacks, P.C.

[57] ABSTRACT

The present invention relates to the use of the decapeptide having the amino acid sequence of SEQ ID NO.:1

Tyr—Leu—Gly—Tyr—Leu—Glu—Gln—Leu—Leu—Arg
1                       5                                10 in the preparation of medicines having benzodiazepine-type activity, particularly useful for the treatment of convulsions and anxiety. The invention also relates to phamaceutical compositions, food supplements, and foodstuffs for special diets containing the said decapeptide.

4 Claims, 4 Drawing Sheets

FIG.1

C18 column with acetonitrile gradient

FIG.2

C4 column
in isocratic conditions
at 25 % acetonitrile

The bars correspond to the mean ± SDM (Standard deviation on mean), except for latency
C1, C2 : controls
D1 : dose 3 mg/kg.
(*) : p < 0.04.
(**) : p < 0.01.

FIG.6

Percentage (± SDM) of entries to open branches as a function of type of treatment
CTR : control, DZP : diazepam, HT : trypsin hydrolysate of $\alpha_{s1}$ casein.
(*) : significant difference ($p < 0.05$).

FIG.7

Number of entries (± SDM) to open branches (BO) and to closes branches (BF) as a function of type of treatment
CTR : control, DZP : diazepam, HT : trypsin hydrolysate of $\alpha_{s1}$ casein.
(**) : significant difference ($p < 0.02$).

Time spent (± SDM) to open branches as a function of type of treatment
CTR : control, DZP : diazepam, HT : trypsin hydrolysate of $\alpha_{s1}$ casein.
(**) : significant difference (p < 0.02).

FIG.8

USE OF A DECAPEPTIDE WITH BENZODIAZEPINE-TYPE ACTIVITY FOR PREPARING MEDICINES AND FOOD SUPPLEMENTS

The present invention relates to the use of a decapeptide of $\alpha_{s1}$ casein for preparing medicines and food supplements.

BACKGROUND OF THE INVENTION

Whole casein is a collection of milk proteins that has been studied in depth, e.g. by Ribadeau-Dumas (1). Chromatography on DEAE-cellulose, separates casein into main fractions which are respectively named: γcaseins, κ casein, β casein, αs1 casein, and αs2 casein. The amino acid sequences of those caseins are well known; in particular the sequence of αs1 casein has been determined by Mercier et al. (2) and by Nagao et al. (3).

It is already known that certain peptide fragments of those various caseins have various biological activities and in particular opiate or anti-opiate activities. Thus, peptides 90–96, 90–95, 91–96, and 91–95 of αs1 casein have opiate activity [Zioudrou et al. (4) and Loukas et al. (5)].

The Applicant has investigated other types of activity of αs1 casein and fragments thereof, in particular benzodiazepine-type activity.

The term "benzodiazepine-type activity" is used, in particular, for anti-convulsive and anxiolytic properties.

OBJECTS AND SUMMARY OF THE INVENTION

It has been found by in vitro tests on the benzodiazepine receptor and by in vivo behavioral tests on the rat that the decapeptide defined below and the total trypsin hydrolysate containing it have advantageous anti-convulsive and anxiolytic properties.

Thus, the present invention provides the use of the decapeptide having the amino acid sequence of SEQ ID NO.:1 in the preparation of medication having benzodiazepine-type activity, in particular for the treatment of convulsions and of anxiety.

The invention also provides pharmaceutical compositions containing an effective quantity of said decapeptide as an active ingredient in combination with a pharmaceutically acceptable vehicle.

The invention also relates to food supplements containing said decapeptide or the total trypsin hydrolysate of αs1 casein containing said decapeptide or a fraction of said hydrolysate containing said decapeptide as an active principle. These food supplements are suitable for adding to the food in particular for people subject to convulsions or to anxiety.

The decapeptide having the amino acid sequence of SEQ ID NO.:1 of molecular mass 1267 Da, corresponds to the peptide 91–100 of αs1 casein.

It can be obtained from αs1 casein by enzymatic hydrolysis, in particular by using trypsin. It can subsequently be concentrated or isolated by inverse phase high performance liquid chromatography (HPLC), by anion exchange high performance liquid chromatography or by gel filtration chromatography with a threshold of 1800 Da, or by centrifuging on a membrane, and other membrane separation techniques (microfiltration, ultrafiltration, etc.).

The decapeptide may also be obtained by peptide synthesis using methods well known to the person skilled in the art, such as those described by Merrifield (6), for example.

Whole casein is obtained from milk by acid precipitation and neutralization using an alkali in application of well-known methods. For example, it is possible to use the method of Nitschmann et al. (7).

The αs1 casein used as the starting material for obtaining total trypsin hydrolysate and decapeptide according to the invention may be obtained by conventional methods well known to the person skilled in the art from milk, whole caseins, caseinates, and concentrates of total milk proteins, e.g. obtained in application of the methods described by Thomson (8) and Maubois (9).

For example, it is possible to prepare αs1 casein by implementing the method described by Sanogo et al. (10). That method is a fractionation method on DEAE-cellulose using a discontinuous gradient of calcium chloride as eluent. It has the advantage of fractionating all of the caseins quickly. It may advantageously be implemented using DEAE-cellulose DE 52 [as sold by Whatman Ltd., Springfield, Great Britain] as the anion exchange support, which material is a pre-swollen resin requiring no acid-base pre-treatment prior to first use.

By using another type of DEAE-cellulose resin, it is possible to eliminate all caseins other than αs1 casein in two steps only, while increasing the purity and the yield of the αs1 casein obtained. Thus, for example, it is possible to use a dry resin instead of a pre-swollen resin, e.g. DEAE-cellulose DE 23 [sold by Whatman cited above]. By using a dry resin and omitting the pre-treatment required for obtaining a maximum load, the effectiveness of the load of the resin is limited, thereby limiting fixation of the substrate thereon.

Medicines useful for treating convulsions or anxiety prepared with the decapeptide defined by the invention may be administered by various routes, e.g. orally or parenterally.

For oral administration, pharmaceutical compositions of the invention may be in the form of tablets, capsules, powders, granulates, or any other form suitable for oral administration.

Pharmaceutical compositions of the invention may also contain acceptable pharmaceutical vehicles commonly used for oral preparations.

For parenteral administration, it is possible to use isotonic saline solutions, and injectable solutions that may contain compatible dispersion agents.

The total trypsin hydrolysate obtained by the action of trypsin on αs1 casein under the above-indicated conditions comprises 5% to 6% by weight of the 91–100 peptide.

It may be used as an active principle either in food supplements in combination with protein or glucide food media, or else in foodstuffs for special diets.

MORE DETAILED DESCRIPTION

The invention is described below in greater detail by the following non-limiting examples.

EXAMPLE 1 preparing the 91–100 pentide of $\alpha_{s1}$ casein ((f91–100)-CN$\alpha_{s1}$ peptide)

A - Preparation of $\alpha_{s1}$ casein 5 g of sodium caseinate were dissolved in 100 ml of 20 mM acetate buffer, pH=6.6, containing 3.3 M of urea, 35 mM of EDTA, and 0.1% of 2-mercaptoethanol, then 20 g of DE 23 DEAE-cellulose resin equilibrated in 150 ml of the same buffer were added, and the resulting mixture was stirred for about 15 min. at 25° C. It was filtered through a Büchner funnel and then the retentate was eluted with twice 250 ml of acetate-urea-EDTA buffer. The first filtration allowed to eliminate a fraction FI containing γ, κ and β caseins. Thereafter 250 ml of acetate-urea buffer containing 35 mM of CaCl2 was added and the above operation was repeated; which thus allowed to eliminate a second fraction FII which contained $\alpha$s2 casein. The above extraction was repeated using an acetate-urea buffer containing 70 mM of CaCl2 and a third fraction FIII was isolated containing the $\alpha$s1 casein.

At the end of the procedure, the resin was washed with the initial buffer and stored at +4° C. in said solution containing 0.2% of sodium azide. Stored in this way, the resin can be used again directly without regeneration for another extraction.

After being dialyzed against ultrapure water and then freeze-dried, the filtrates FI, FII, and FIII were subjected to polyacrylamide-urea gel electrophoresis in order to see the fractionation.

In the absence of CaCl2, the γ, κ, and β caseins were eluted (FI). The $\alpha$s2 casein was released by CaCl2 at a concentration of 35 mM (FII). The third fraction (FIII) eluted at a CaCl2 concentration of 70 mM contained $\alpha$s1 and $\alpha$s0 caseins. The latter is merely a minor form of $\alpha$s1 casein, differing from the major form by the presence of an additional phosphate group in position 41.

The purity of the asi casein obtained in this way was greater than 96%. It was used as such in the remainder of the method without an additional purification step.

B - Preparing the trypsin hydrolysate of $\alpha_{s1}$ casein

Trypsin hydrolysis of $\alpha$s1 casein at a concentration of 0.2% (w/v) in 25 ml of NH3/HCOOH buffer (57 mM/43 mM) pH=8.5 at 37° C. was performed with bovine pancreatic trypsin fixed on beads of agarose and treated with N-tosyl L-Phe chloromethyl ketone (TPCK) (80 units/ml of beads) as the enzyme. An enzyme concentration was chosen equal to 8.5 units of the ethyl ester of Na-benzoyl-L-arginine and a hydrolysis time was chosen equal to one hour followed by centrifuging at +4° C. for 5 min. at 1800 g.

Two enzyme aliquots were taken to perform two hydrolysis operations in parallel. The supernatant liquids from the hydrolyses, centrifuged to remove the insoluble enzyme, were mixed together again. Evaporation was performed nine times interspersed with washing with water. After the last evaporation, the hydrolysate, thus free of the major portion of its salts, was taken up in a minimum of water, freeze-dried, and stored at −30° C.

C—Inverse phase HPLC fractionation with an acetonitrile gradient and under isocratic conditions The casein hydrolysate obtained in step B was subjected to two purification steps.

$C_1$—purification on $C_{18}$ column

The first purification step was a fractionation of the $\alpha$s1 casein trypsin hydrolysate in inverse phase HPLC on a C18 column (Merck, Darmstadt, Germany) 250 mm×4 mm, 100 Å, 5 μm, using a gradient of acetonitrile in water (in the presence of 0.1% trifluoroacetic acid or TFA) passing from 5% acetonitrile to 40% in 70 minutes.

The peak which was eluted at around 61 min. (about 32% v/v acetonitrile) and containing amongst others the (f91–100)-CN$\alpha_{s1}$ peptide was collected. The acetonitrile and the TFA were evaporated off under reduced pressure prior to freeze-drying.

$C_2$—purification on a $C_4$ column

The previously collected peak was then purified by inverse phase HPLC using a Delta Pak C4 column 150 mm×3.9 mm, 300 Å, 5 pm (Waters, Midford, UK) under isocratic conditions of acetonitrile at 25% v/v in water and in the presence of 0.1% TFA. The (f91–100)-CN$\alpha_{s1}$ peptide was eluted at about 10 min. It was collected and freeze-dried. The lyophilizate was taken up in water and freeze-dried again.

Figure 1:
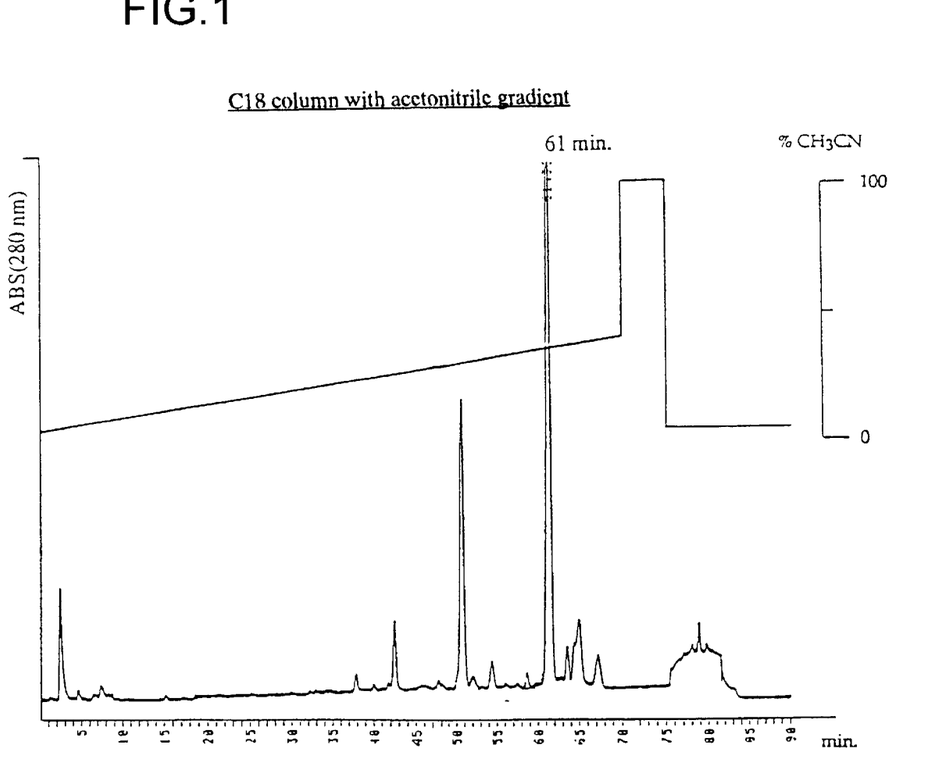
FIG. 1 is an HPLC chromatogramn depicting the purification of the casein hydrolysate on a $C_{18}$ column with an with an acetonitile gradient.
Figure 2:
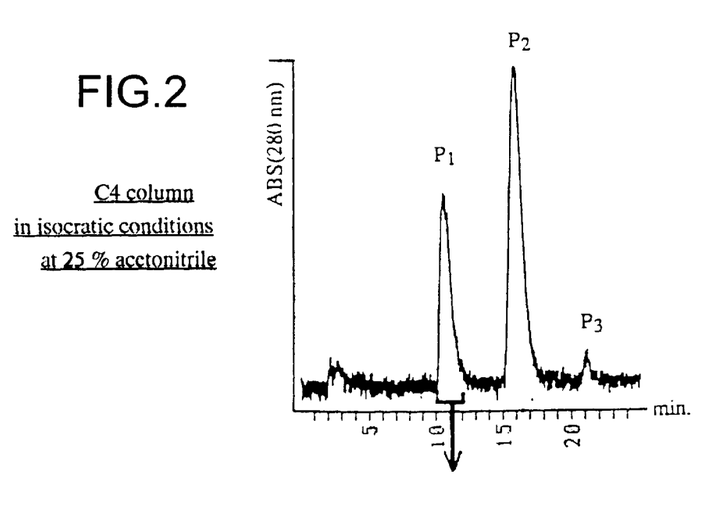
FIG. 2 is an HPLC chromatograni depicting the second phase of the purification using a $C_4$ colun inlL isocratic mode at 25% acetonitrile.

The nature of the peptide was confirmed by fast atom bombardment (FAB) or electron bombardment mass spectrometry (measured molecular mass=1267.1 Da) and by its amino acid composition determined by the ninhydrin method of Hamilton et al. (11). The elution profiles from the C18 and C4 columns are shown in FIGS. 1 and 2 respectively in which absorbance at 280 nm is plotted up the ordinate and elution time along the abscissa.

EXAMPLE 2 obtaining fractions enriched in the (f91–100)-CN$\alpha_{s1}$ peptide by different routes A—Fractionation of $\alpha_{s1}$ casein trypsin hydrolysate by membrane centrifuging For the purpose of quick pre-purification of casein trypsin hydrolysate, coarse fractionation was performed by centrifuging on a membrane with a mean cutoff threshold of 2000 Da (Amicon YM1).

2 mg of the product obtained from Example 1 (step B) dissolved in 1 ml of ultrapure water were placed in an MPS-1 type Amicon micropartition system. The centrifuging time was 40 min. or 60 min. in an acceleration field of 3900 g.

At the end of the centrifuging time, the two micropartition systems were removed from the centrifuge and the permeates and retentates were stored in microtubes. The contents of the various microtubes were then freeze-dried.

The (f91–100)-CN$\alpha_{s1}$ peptide was of small molecular mass and passed through the membrane, so it was found in the permeate.

B—Fractionation of $\alpha_{s1}$ casein trypsin hydrolysate by anion exchange high performance liquid chromatography (MONO Q, HR 5/5)

By using an FPLC chromatography system (Pharmacia Uppsala, Sweden) it was possible to obtain much finer separation of the peptides, but only at a semi-preparative level (injection of 1 mg to 2 mg of asi casein trypsin hydrolysate).

The hydrolysate obtained in Example I (step B) was fractionated by a gradient of 0 to 30% of B in A for 45 min., then 30% to 100% of B in A for 30 min. (A:Tris-HCl 20 mM, pH 8.0; B: Tris-HCl 20 mM, pH 8.0 with 350 mM of NaCl). The (f91–100)-CN$\alpha_{s1}$ peptide of small molecular weight and having a small number of charged amino acids was eluted in the fraction corresponding to the dead volume.

C—Fractionation of $\alpha_{s1}$ casein trypsin hydrolysate by gel filtration chromatography with a threshold of 1800 Da Five to ten milligrams of hydrolysate were placed on a bed of Biogel P2 gel (Pharmacia Uppsala, Sweden) (diameter 1 cm, height 40 cm). Elution was performed under atmospheric pressure with ultrapure water at a rate of 5 ml/h to 10 ml/h.

Two fractions (F1 and F2) were thus obtained. Fraction F1 contained the peptides excluded from the gel (molecular mass greater than 1800 Da) and fraction F2 contained the peptides filtered by the gel (including the (f91–100)-CN$\alpha_1$ peptide).

PHARMACOLOGICAL TESTS

A—IN VITRO TESTS ON THE BENZODIAZEPINE RECEPTOR

The experiment was performed by means of a kit sold by Dupont de Nemours (NENQUEST TM, Drug Discovery System, NED-002). The method is based on competition between a radioactive ligand of the central benzodiazepine receptor and the molecule to be tested. If the molecule has an affinity for the receptor, it displaces the labelled ligand fixed to the receptor. Such displacement of the ligand as a function of the added concentration of the molecule to be tested makes it possible to determine the IC50 of the molecule, i.e. the pharmacological concentration which enables 50% of the maximum effect to be obtained.

The ligand used was $^3$H-methyl-flunitrazepam, a benzodiazepine that possesses high specificity for the receptor (Ki=1.2 nM) and low aspecific fixation. Commercial membrane preparations of central receptors of benzodiazepines were incubated with increasing concentrations of the sample to be tested and a fixed concentration of radioligand. Incubation lasted one hour at +4° C. The temperature was deliberately chosen to be low so as to limit association/dissociation between the receptor and the radioligand. Flunitrazepam has a half-association time of 834 s at 0° C. and of 12 s at 35° C. (Speth et al. (12)). After one hour, the mixture was passed through a Whatman GF/B filter. Such filters retain the membranes and the ligands fixed thereto (benzodiazepines, peptide fragment(s) of $\alpha$s1 casein trypsin hydrolysate). After washing, the filters were placed in scintillation counter flasks containing a scintillation liquid. The emission of β rays was counted by a liquid scintillation counter.

If the tritium-labelled ligand has been displaced by the molecule under test, then a drop is observed in the level of radioactivity present on the filter.

In order to eliminate radioactivity due to an aspecific bond between the tritium-labelled ligand and the receptor, a test was performed by incubating the membranes, the tritium-labelled ligand at the same concentration as that used for the tests on a molecule whose IC50 is to be determined, and un-labelled flunitrazepam at an excess concentration of 500 times. The residual radioactivity was thus due only to aspecific fixation since it was assumed that all of the sites were occupied by un-labelled flunitrazepam.

A value B can be defined equal to the percentage of radioactivity fixed on the receptors for each concentration of the molecule under test compared with a test performed using the membranes and the labelled flunitrazepam only (maximum radioactivity). It is possible to determine the IC50 of the molecule by plotting the base-10 logarithm of B/(100-B) as a function of the base-10 logarithm of the concentration of the added molecule under test.

The lower a value of IC50, the higher the affinity of the molecule for the receptor. For total trypsin hydrolysate of $\alpha$s1 casein (not purified), the best IC50 relative to the central benzodiazepine receptor that has been found so far is 78 $\mu$M.

For the (f91–100)-CN$\alpha_{s1}$ peptide purified by the method described in Example 1, step C, IC50 is about 88 $\mu$M.

These tests have also been performed using the decapeptide obtained by peptide synthesis according to Merrifield (6). It was found that the IC50 of the synthesized peptide was 370 $\mu$M compared with 88 $\mu$M for the decapeptide of natural origin.

Activity was also found for fractions enriched with the (f91–100)-CN$\alpha_{s1}$ peptide in application of the methods described in Example 2.

B—IN VIVO TESTS ON THE WISTAR RAT

B1—Anti-convulsive activity

Pentylenetetrazol is a molecule acting on chloride channels of the GABA A receptor. By blocking this type of channel, it produces symptoms resembling those of an epileptic seizure. Molecules of the anti-epilepsy type oppose this effect by reducing the consequences due to the presence of pentylenetetrazol.

The tests were performed in the rat holding room during a period of darkness. The quantity of $\alpha$s1 casein trypsin hydrolysate (D1) injected was 3 mg/kg of rat bodyweight. The injection route used was the intraperitoneal route. The total trypsin hydrolysate was placed in solution in 25% dimethyl isosorbide ether in water; this mixture has the advantage of being amphiphilic. Dimethyl isosorbide ether is miscible in water and has the advantage of dissolving molecules that are very hydrophobic.

Three parameters were studied in order to describe the importance of the seizure:

Severity of the seizure was evaluated using Racine's scale (13).

Stage 0: no visible behavioral response.

Stage 1: increased immobility of the animal.

Stage 2: rocking of the head and/or clonic movements of the jaw.

Stage 3: stage 2 +standing on the back paws.

Stage 4: stage 3 +clonic movements of the front paws.

Stage 5: full seizure. Standing on the back paws, clonus of the front paws and of the face, loss of balance.

Latency which is the time in seconds between injection of pentylenetetrazol and the appearance of the first sign of seizure.

Duration which is the time in seconds between the first and last signs of seizure.

Figure 3:
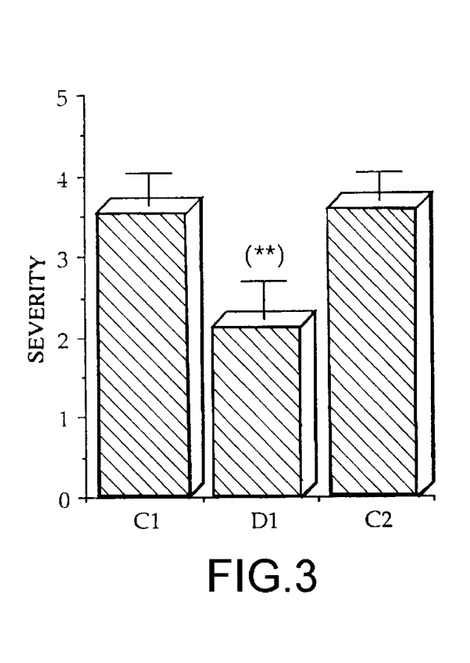
FIG. 3 is a bar graph demonstrating the severity of a seizure in a rat epileptic model after administration of the casein hydrolysate as compared to two controls (C1 and C2)
Figure 4:
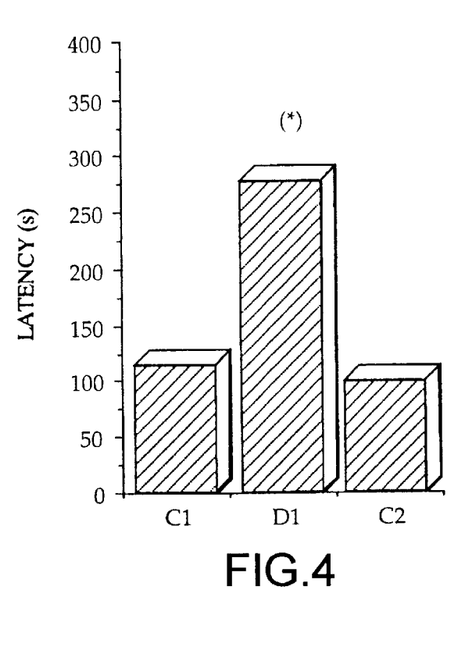
FIG. 4 is a bar graph depicting the latency in seconds between injection of pentylenetetrazol and the appearance of the first signs of a seizure in the same rat model of epileptic seizure.
Figure 5:
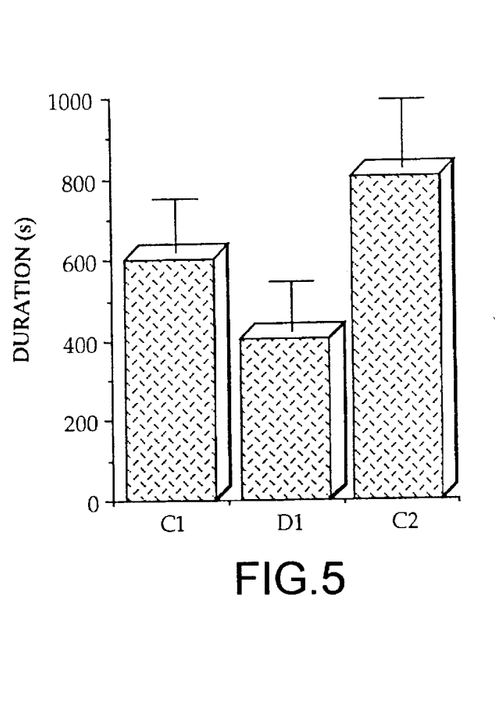
FIG. 5 is a bar graph depicting the duration of the epileptic seizure in seconds between the first and last signals of the seizure in the same rat model of epileptic seizures.

The results obtained with total trypsin hydrolysate are given in FIGS. 3, 4, and 5 which show respectively:

severity (FIG. 3)

latency (FIG. 4)

duration (FIG. 5)

For severity, the controls performed (C1 and C2) show relative consistency, thus validating the observations performed with the hydrolysate. With the injected dose of trypsin hydrolysate (3 mg/kg), considerable reduction in the severity of the seizure was observed. Averages went from 3.53±0.40 to 2.13±0.47. Statistical analysis using the Wilcoxon test taking the control prior to the hydrolysate test as the reference, gave a significant trend with Z=2.69 (p<0.01) towards a reduction of seizure (40% reduction). By returning to the level of the preceding control, the control performed after the hydrolysate test demonstrated that the observed reduction in severity with hydrolysate was not due to a phenomenon of repetition or of accustomization.

For latency, with a dose of 3 mg/kg, median times went from 114 s for the prior control to 277 s. With Z=2.17 (p<0.04) this corresponded to a significant trend in increasing the time between injection of pentylenetetrazol and the first behavioral sign of seizure.

With duration, injection of 3 mg/kg of $\alpha$s1 casein of trypsin hydrolysate seemed to give rise to a reduction in the duration of the seizure; however, this reduction (602±130 s to 404±123 s) is not significant (Z=1.10). The injected substance had a protective effect since pentylenetetrazol gives rise to seizures that are weaker, that are delayed, and that appear to be shorter in duration. The effect is analogous to that of substances which potentialize a GABA-like action such as benzodiazepines.

B2—Tranquilizing activity

To measure anxiety in the rat, the elevated plus-maze test described by Pellow et al. (14) was used which is based on neophobia in the rat. The plus-maze had four branches that were 50 cm long and 10 cm wide. The two closed branches were surrounded by walls that were 25 cm high (the top being left open for observation) and the entire maze was 50 cm above the ground. The center of the maze communicated with the two open arms and the two closed arms. In dim light, the less anxious the rat, the more the rat will tend to explore the open arms, which does not correspond to natural behavior.

The number of times the animal enters the open arms, the closed arms, and the total number of times the rat enters the arms are important parameters. The time passed in each type of branch was also measured. Other parameters (a total of 22) such as the number of times the rat stood up, the number of times it groomed itself (signs of anxiety), or latency of first entry into an open or closed branch were taken into account. The animal was observed for 5 minutes after being placed in the center of the apparatus. Its entire behavior was filmed by video camera, which procedure served to avoid errors.

Observations were performed on a control group of 20 rats (CTR), on a positive control group comprising 20 rats that received 2 mg/kg of diazepam (DZP), and on a group of 20 rats that were treated with 3 mg/kg of trypsin hydrolysate of $\alpha$s1 casein (HT), (which dose was determined from the convulsion experiment).

The control group (CTR) received an intraperitoneal injection of solvent only, which solvent was a mixture of gelatin and mannitol (0.5%/5%) dissolved in water. The mixture serves to place diazepam into suspension, given that diazepam is insoluble in conventional injectable solvents (water, NaCl 9%, ethanol 10%). The animals in all of the groups were injected half an hour before going to the plus-maze. To begin the experiments, each rat was placed in the center of the apparatus.

Figure 6:
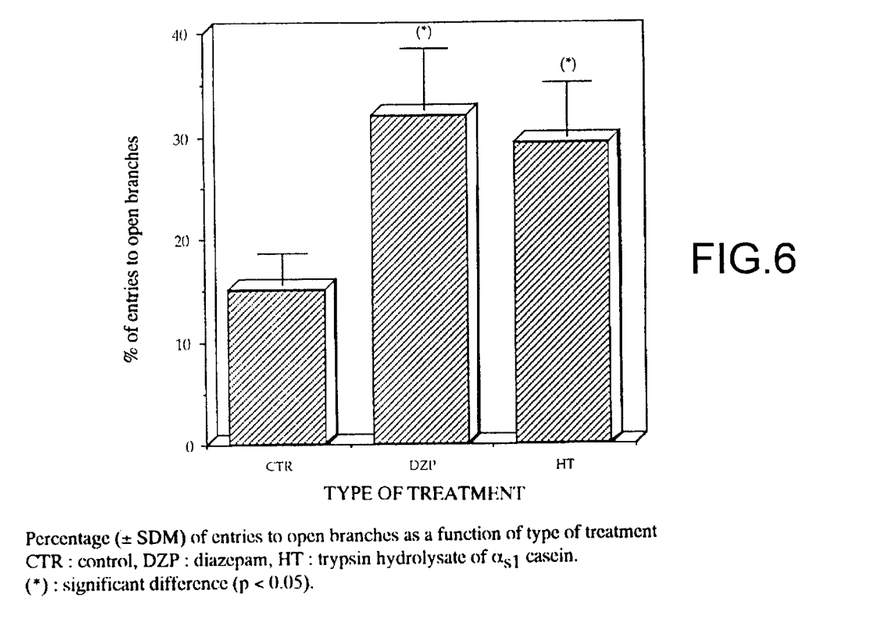
FIG. 6 is a bar graph depicting the tranquilizing effect of the casein hydrolysate in rats subjected to an elevated plus/maze test in terns of the number of open branches entered by the rat.
Figure 7:
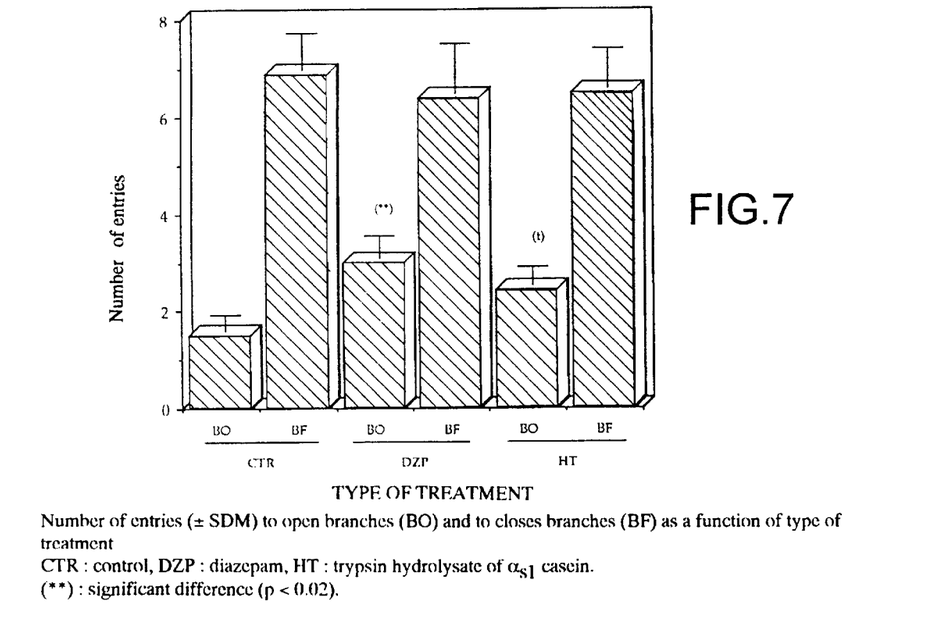
FIG. 7 is a bar graph depicting the tranquilizing effect of the casein hydrolysate in the same rat model as FIG. 6, but examining the number of entries into open branches (BO) and closed branches (BP)
Figure 8:
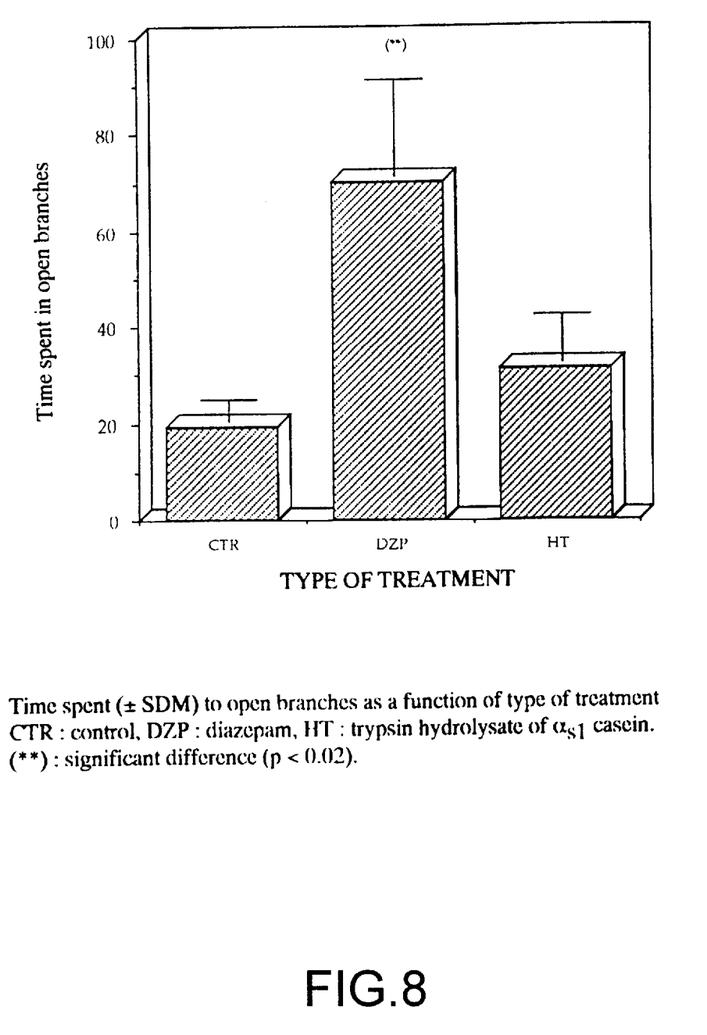
FIG. 8 is a bar graph depicting the tranquilizing effect of the casein hydrolysate in the same rat model as FIG. 6, but defining the time spent in the open branches.

The results are given in FIGS. 6, 7, and 8, which show, as a function of the type of treatment:

the percentage of entries into open branches (FIG. 6);

the number of entries into open branches (BO) and into closed branches (BF) (FIG. 7); and the time spent in the open branches (FIG. 8).

Rats treated with diazepam (DZP) performed 32.1±5.9% of their entries into open branches, whereas the controls performed only 15.1±3.0% (p<0.05). For rats treated with the hydrolysate (HT), 29.3±5.3% of their entries were to open branches (p<0.05). It should be observed that it was the number of entries into open branches that increased with diazepam (3.0±0.4) and hydrolysate (2.4±0.4) (control: 1.5±0.3) whereas the number of entries into closed branches did not vary significantly.

Rats treated with diazepam spent longer in the open branches (70.1±19.9 s; p<0.02) than did the controls (19.3±4.4 s). For rats treated with the hydrolysate (31.1±10.1 s) the increase relative to the control group is not statistically significant.

It can therefore be concluded that in this test, and studying major parameters only, trypsin hydrolysate of $\alpha$s1 casein had an action comparable to that of diazepam but with a smaller effect; this is not surprising since the crude hydrolysate was used.

Bibliographic references (1) RIBADEAU-DUMAS, B., 1991, Physicochimie et biochimie des prot6ines du lait. Donnees recentes, Lait, 71, 133–139.

(2) MERCIER, J. C., GROSCLAUDE, F., and RIBADEAU-DUMAS, B., 1971, Structure primaire de la casfine asl bovine. Sequence complete, Eur. J. Biochem., 2, 41–51.

(3) NAGAO, M., MAKI, M., SASAKI, R., and CHIBA, H., 1984, Isolation and sequence analysis of bovine asl-casein cDNA clone, Agric. Biol. Chem., 48, 1663–1667.

(4) ZIOUDROU C., STREATY, R. A., and KLEE, W. A., 1979, Opioid peptides derived from food proteins: the exorphins, J. Biol. Chem., 2, 2446–2449.

(5) LOUKAS, S., VAROUCHA, D., ZIOUDROU, C., STREATY, R. A., and KLEE, W. A., 1983, Opioid activities and struure of $\alpha$-casein-derived exorphins, Biochemistry, 2, 4567–4573.

(6) MERRIFIELD, R. B., 1963, Solid phase peptide synthesis I. Synthesis of a tetrapeptide, J. Amer. Chem. Soc., 85, 2149–2154.

(7) NITSCHMANN, H. S., and LEHMANN, W., 1947 Zum Problem der Labwirkung auf Casein, Helv. Chim. Acta, 130, 804.

(8) THOMSON, A. R., 1984, Recent developments in protein recovery and purification, J. Chem. Tech. Biotechnol., 34B, 190–198.

(9) MAUBOIS, J. L., 1984, Separation extraction and fractionation of milk protein components, Lait, LA, 485–495.

(10) SANOGO, T., PAQUET, D., AUBERT, F., and LINDEN, G., 1989, Purification of asl-casein by fast protein liquid chromatography, J. Dairy Sci., 7, 2242–2246.

(11) HAMILTON, P. B., 1963, Ion exchange chromatography of amino acids. A single column, high resolving, fully automatic procedure, Anal. Chem., 3, 2055–2063.

(12) SPETH, R. C., WASTEK, G. J., and YAMAMURA, H. I., 1978, Benzodiazepines binding in human brain characterization using $^3$H flunitrazepam, Life Sci., Ad, 859–866.

(13) RACINE, R. J., 1972, Modification of seizure activity by electrical stimulation. II. Motor seizure, Electroenceph. Clin. Neurophysiol., 32, 281–294.

(14) PELLOW, S., CHOPIN, P., FILE, S. E., and BRILEY, M., 1985, Validation of open/closed arm entries in an elevated plus-maze as a measure of anxiety in the rat, J. Neurosci. Methods, 41, 149–167.

We claim:

1. A method for treating convulsions and anxiety, comprising:

administering to a subject having convulsions or anxiety a pharmaceutical composition having benzodiazepine type activity and including the amino acid sequence of SEQ ID No. 1:

Tyr—Leu—Gly—Tyr—Leu—Glu—Gln—Leu—Leu—Arg.
1     5        10

2. A pharmaceutical composition, comprising:

an effective amount for the statement of convulsions or anxiety of the decapeptide having the amino acid sequence of SEQ. ID.No. 1:

Tyr—Leu—Gly—Tyr—Leu—Glu—Gln—Leu—Leu—Arg
1     5        10 in combination with a pharmaceutically acceptable vehicle.

3. A food supplement, comprising:

an effective amount for the treatment of convulsions or anxiety of the decapeptide having the amino acid sequence of SEQ ID No. 1:

Tyr—Leu—Gly—Tyr—Leu—Glu—Gln—Leu—Leu—Arg
1     5        10 or a total trypsin hydrolysate of αs1 casein containing it or a fraction of said hydrolysate containing it in combination with protein or sugar type food media.

4. A foodstuff for a special diet, comprising:

an effective amount for the treatment of convulsion or anxiety of the decapeptide having the amino acid sequence of SEQ ID No. 1.:

Tyr—Leu—Gly—Tyr—Leu—Glu—Gln—Leu—Leu—Arg
1     5        10 or a total trypsin hydrolysate of αs1 casein containing it or a fraction of said hydrolysate containing it in combination with protein or sugar type food media.

* * * * *

UNITED STATES PATENT AND TRADEMARK OFFICE
CERTIFICATE OF CORRECTION

PATENT NO. : 5,846,939
DATED : December 8, 1998
INVENTOR(S) : Laurent Miclo, et. al.

It is certified that error appears in the above-identified patent and that said Letters Patent is hereby corrected as shown below:

| | |
|---|---|
| Col. 2, line 62, should read | "chromatogram" |
| Col. 2, line 65, should read | "chromatogram" |
| Col. 2, line 66, should read | "column in" |
| Col. 3, line 14, should read | "terms" |
| Col. 3, line 65, should read | "α s1 casein" |
| Col. 4, line 8, should read | "Nα-benzoyl-L-arginine" |
| Col. 5, line 12, should read | "α s1 casein" |
| Col. 7, line 62, should read | "NaCl9%" |
| Col. 9, line 39, should read | "treatment" |

Signed and Sealed this

Twenty-seventh Day of June, 2000

Attest:

Q. TODD DICKINSON

*Attesting Officer*   *Director of Patents and Trademarks*

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
  ( A ) LENGTH: 10 amino acids
  ( B ) TYPE: amino acid
  ( C ) STRANDEDNESS: single
  ( D ) TOPOLOGY: linear  ( i i ) MOLECULE TYPE: peptide  ( i i i ) HYPOTHETICAL: NO  ( i v ) ANTI-SENSE: NO  ( v ) FRAGMENT TYPE: internal  ( x i ) SEQUENCE DESCRIPTION: SEQ ID NO:1:

Tyr Leu Gly Tyr Leu Glu Gln Leu Leu Arg
 1        5            10